United States Patent [19]

Cincotta et al.

[11] 4,290,955

[45] Sep. 22, 1981

[54] 3,6-DI(ALKYL/PHENYL)AMINO-9-CARBOXAMIDOPHENYL-XANTHENES

[75] Inventors: Louis Cincotta; James W. Foley, both of Andover, Mass.

[73] Assignee: Polaroid Corporation, Cambridge, Mass.

[21] Appl. No.: 154,620

[22] Filed: May 30, 1980

Related U.S. Application Data

[62] Division of Ser. No. 106,902, Dec. 26, 1979.

[51] Int. Cl.³ .......................................... C07D 311/82
[52] U.S. Cl. .................................. 260/336; 430/221;
260/335; 260/325 R; 548/207
[58] Field of Search .............................. 260/335, 336

[56] References Cited

U.S. PATENT DOCUMENTS

| | | | |
|---|---|---|---|
| 1,879,537 | 9/1932 | Schneider | 430/517 |
| 1,994,876 | 3/1935 | Schneider et al. | 430/514 |
| 2,182,794 | 12/1939 | Dawson | 430/513 |
| 2,203,767 | 6/1940 | Baldsiefen | 430/514 |
| 2,203,768 | 6/1940 | Baldsiefen | 430/515 |
| 2,350,090 | 5/1944 | Beilenson | 430/514 |
| 3,005,711 | 10/1961 | Burgardt et al. | 430/520 |
| 3,406,069 | 10/1968 | Overman | 430/507 |
| 3,615,548 | 10/1971 | Chai | 430/522 X |
| 3,713,770 | 1/1973 | Mundlos et al. | 260/336 X |
| 3,723,116 | 3/1973 | Kinjo et al. | 430/80 |
| 3,849,065 | 11/1974 | Schmeidl | 260/336 X |
| 3,883,529 | 5/1975 | Austin | 544/85 |
| 3,922,283 | 11/1975 | Yahagi et al. | 260/336 X |
| 4,178,446 | 12/1979 | Bloom et al. | 544/33 |

OTHER PUBLICATIONS

Beilstein's Handbuch der Organischer Chemie, vol. 27, p. 534, (1937).

*Primary Examiner*—Joseph Paul Brust
*Attorney, Agent, or Firm*—Sybil A. Campbell

[57] ABSTRACT

In one embodiment, the present invention is concerned with novel xanthene compounds of the formula

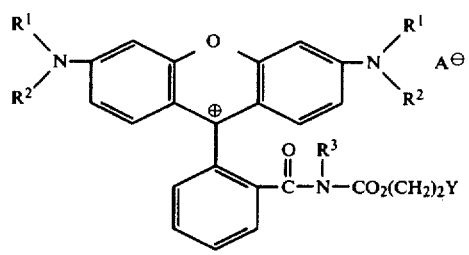

wherein each $R^1$ the same or different is hydrogen or alkyl, each $R^2$ the same or different is alkyl or phenyl, $R^3$ is phenyl or alkyl, Y is an electron-withdrawing group and A is an anion. In another embodiment, the present invention is concerned with photographic products and processes employing these xanthene compounds.

6 Claims, 2 Drawing Figures

3,6-DI(ALKYL/PHENYL)AMINO-9-CARBOXAMIDOPHENYL-XANTHENES

This is a division of application Ser. No. 106,902, filed Dec. 26, 1979.

BACKGROUND OF THE INVENTION

1. Field of the Invention

This invention relates to novel xanthene compounds and to their use, e.g., as light-screening dyes in photographic products and processes.

2. Description of the Prior Art

It is well known that photographic film, and especially multicolor films, may and generally do vary from lot to lot, notwithstanding efforts to "repeat" previous films. Manufacturers of multicolor photographic films have developed a number of procedures to minimize the effects upon the final multicolor image of unavoidable variations in the manufacturing operations. These variations are reflected primarily in shifts in color balance as reflected in mismatching of the D log E curves of the individual red, green and blue exposures. Equipment used to coat multicolor films is highly precise but variations between intended coverage of silver halide and/or the dye image-forming materials do occur. Repeat batches of silver halide emulsions may, and usually do, vary in their photographic response. Individual layers may be dried to slightly different degrees. Films may be stored for a period of time after coating to allow the films to "age", so that changes in sensitometry following coating have an opportunity to reach a plateau prior to sale. If the film is designed to be developed by a photofinisher or in a darkroom, processing of the exposed multicolor film is controlled within very narrow limits, typically within plus or minus a half degree of a prescribed temperature, in order to minimize sensitometric variations from film to film. Where the multicolor film is of the negative type, an opportunity to adjust the sensitometry occurs in printing the desired final positive image, during which operation the printing exposure may be appropriately color filtered.

The basic sources of sensitometric variations noted above exist also in multicolor diffusion transfer work, with the added complication that once the film is shipped, the sensitometric properties are essentially fixed. The opportunity for adjustment provided in darkroom processing, practically speaking, is unavailable for users of self-developing films. While professional and advanced amateur photographers may be skillful enough to utilize color correction filters to at least partially "rebalance" the color balance, ordinary users of the film would only be confused by such additional operations.

It is well known to use light-screening dyes in photographic elements. Such a dye may be incorporated as a filter dye in a light-sensitive emulsion layer(s) or in a layer coated over one or more light-sensitive emulsion layers or between two differently color-sensitized emulsion layers to modify the light record in the emulsion layer or to control the spectral composition of light falling on the underlying light-sensitive layer, or it may be incorporated as an anti-halation dye in a non-light-sensitive layer positioned on either side of a support carrying the light-sensitive layer(s).

The dyes employed for these purposes, in addition to having the requisite spectral absorption characteristics for their intended use, should be photochemically inert, that is, they should not have any adverse effect on the properties of the light-sensitive emulsion layer(s), and also, they should be capable of being decolorized or removed during photographic processing so as not to leave stain in the processed photographic element. In photographic processes where the dye is removed by being dissolved in a processing solution, it is usually preferred that the dye also decolorize in order to avoid contamination of the processing solution and to prevent staining from residual dye in the processed light-sensitive element.

Though various classes of dyes have been proposed for use in antihalation and color correction filter layers, the dyes heretofore employed have not been altogether satisfactory. Some of the dyes tend to reduce sensitivity, fog or exert other adverse effect on the light-sensitive material. However, the major drawback of previously employed dyes is their tendency to cause stain due to incomplete decolorization or reversal of some of the decolorized form to the original colored form. For example, some classes of dyes rely on the presence of a reagent, such as, a sulfite for "bleaching", i.e., decolorization and unless the dyes are removed from the light-sensitive material during or after processing, their color may reappear in time.

Among the classes of light-screening dyes used previously are the triarylmethanes and xanthenes. For example, U.S. Pat. Nos. 1,879,537; 1,994,876; 2,350,090 and 3,005,711 disclose the use of fuchsone-type dyes in antihalation layers, and U.S. Pat. Nos. 3,406,069 and 3,615,548 are concerned with the metal chelates of fuchsone dyes as antihalation dyes. These and other types of triarylmethane dyes suffer from one or more of the drawbacks discussed above, and in particular, prior dyes of this type have been difficult to keep decolorized at the pH's normally encountered during processing subsequent to "bleaching" and in the final product. Xanthenes have been employed in antihalation layers that are removed during photographic processing. For example, U.S. Pat. Nos. 2,182,794; 2,203,767 and 2,203,768 disclose the use of rhodamine dyes in certain antihalation layers that are removed during processing in an acid bath or a plain water rinse bath depending upon the solubility characteristics of the particular layer.

Copending U.S. patent application Ser. No. 106,520 of James W. Foley filed Dec. 26, 1979 is concerned with colored triarylmethane compounds possessing in their triaryl structure a 4'-oxo-1'-naphthylidene/phenylidene moiety, a naphthyl/phenyl moiety and a phenyl moiety substituted in the position ortho to the central carbon atom with a group that undergoes an irreversible cleavage reaction in base to provide a moiety that adds to the central carbon atom to form a new ring-closed compound which is colorless. As disclosed and claimed therein, these compounds are useful as photographic light-screening dyes which offer advantages over prior light-screening dyes because of their ability to decolorize completely and irreversibly to a substantially inert colorless product.

The present invention is concerned with another class of compounds, namely, xanthene compounds which also find utility as photographic light-screening dyes and which also are free from the deficiencies associated with the dyes previously used for this purpose. The subject dyes, which will be defined with greater particularity hereinafter, are efficient absorbers of radiation within a predetermined range in the visible range of 400 to 700 nm, may be incorporated in gelatin or other processing composition-permeable colloidal binding agents and are decolorized at an alkaline pH to yield a colorless product. Because of their ability to decolorize completely and irreversibly in base without requiring an additional reagent, such as, a sulfite for the "bleaching" reaction and because the new colorless product produced upon irreversible cleavage remains colorless in aqueous solution over a pH range of about 4 to 14, the cleavage product normally may be retained in the photographic light-sensitive element without the possibility of color reappearing in time. Besides being non-staining, the compounds usually are substantially inert with respect to the light-sensitive material and thus, may be positioned in a layer adjacent to a silver halide emulsion layer or directly incorporated into an emulsion layer without having any adverse effect on the properties of the emulsion.

Xanthenes of the structure

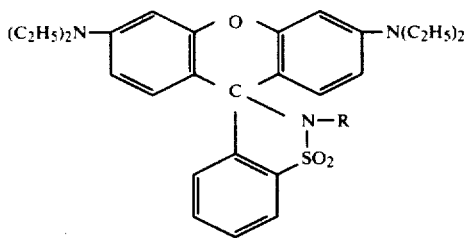

wherein R is H or —$COCH_3$ are disclosed in Beilstein's Handbuch der Organischen Chemie, Vol. 27, p. 534. These compounds are synthesized by condensing m-diethylaminophenol with saccharin at a temperature of 165° C. to give the compound wherein R is H, which compound is then heated to boiling with acetic acid anhydride to yield the N-acylated derivative. As reported therein, solutions of the N-acetyl compound unlike solutions of the N-unsubstituted compound (R=H) are not decolorized by boiling, and the acetyl group splits off only after prolonged boiling with alcoholic sodium hydroxide. Further to the N-unsubstituted compound, it has been found that this compound is colorless at an alkaline pH, faintly colored at neutrality and becomes more intensely colored as the pH is reduced to pH 4.

SUMMARY OF THE INVENTION

It is therefore the primary object of the present invention to provide novel xanthene compounds.

It is another object of the present invention to provide xanthene compounds useful in photographic products and processes.

It is a further object of the present invention to provide photographic products and processes employing said compounds Other objects of this invention will in part be obvious and will in part appear hereinafter.

This invention accordingly comprises the process involving the several steps and the relation and order of one or more of such steps with respect to each of the others and the products and compositions processing the features, properties and the relation of elements which are exemplified in the following detailed disclosure and the scope of the application of which will be indicated in the claims.

According to the present invention, novel xanthene compounds are provided which possess an N-alkyl/aryl group in each of the 3 and 6 positions and a substituted phenyl moiety in the 9 position which moiety has the formula

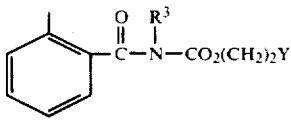

wherein $R^3$ is alkyl or phenyl and Y is an electron-withdrawing group. In another embodiment, photographic products and processes are provided which employ the above-denoted xanthene compounds, which compounds are irreversibly decolorized by forming a new ring-closed compound when contacted with an alkaline photographic processing composition.

For a fuller understanding of the nature and objects of the present invention, reference should be had to the following detailed description taken in conjunction with the accompanying drawings.

DETAILED DESCRIPTION OF THE INVENTION

Figure 1:
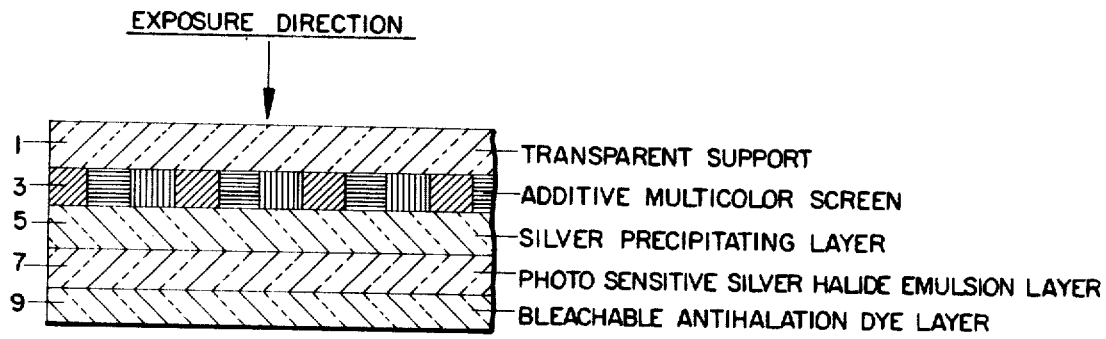
FIG. 1 is a diagrammatic, enlarged cross-sectional view of a diffusion transfer film unit incorporating a xanthene compound of the present invention as a bleachable antihalation dye layer.

Specifically, the compounds employed in accordance with the present invention may be represented by the formula

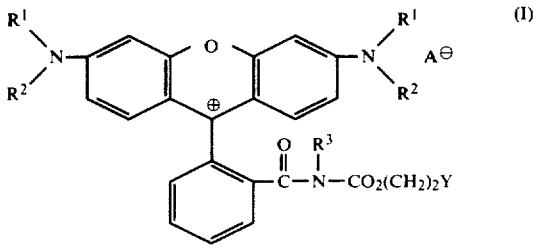

wherein each $R^1$ the same or different is hydrogen or alkyl, each $R^2$ the same or different is alkyl or phenyl, $R^3$ is alkyl or phenyl, Y is an electron-withdrawing group and A is an anion. By "electron-withdrawing group" is meant a group having a positive sigma value as defined by Hammett's Equation.

Typically said $R^1$ and $R^2$ groups, when alkyl, contain 1 to 4 carbon atoms, and $R^3$ is alkyl containing 1 to 4 carbon atoms. Usually said $R^1$ groups are the same, and said $R^2$ groups are the same.

The electron-withdrawing group, Y, preferably has a positive sigma value ($\delta^-$) greater than 0.6. Preferred electron-withdrawing groups include nitro; cyano; —$SO_2CH_3$;

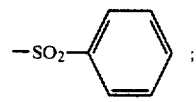

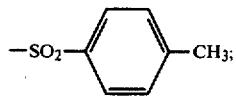

COCH₃; and —SO₂N(CH₂Ph)₂. The sigma value for these and other groups, such as, —CHO, —COOH, —COOC₂H₅ and —CONH₂ have been reported by Eugen Müller, Methoden Der Organischen Chemie, Georg Thieme Verlag, Stuttgart, 1970, p. 78 in terms of δ⁻ values based on the ionization of p-substituted phenols.

The anion associated with the subject xanthene compounds, i.e., A in formula I above may be any of the simple anions, for example, tosylate, sulfate, nitrate, perchlorate, acetate, oxalate, methanesulfonate or halide, such as, chloride or bromide.

It should be understood that other resonance forms of the subject compounds are intended to be encompassed by Formula I.

As noted above, the subject compounds are initially colored, i.e., capable of absorbing visible radiation, and at an alkaline pH, are converted to a colorless product by undergoing an irreversible cleavage reaction with base. The colorless product formed is a new compound which is different from and non-reversible to the colored compound by a change in pH. In particular, it is the

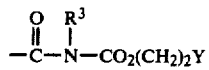

group substituted on the phenyl moiety that undergoes the irreversible cleavage reaction in alkaline solution that is complete within a predetermined time at a predetermined alkaline pH to give the new colorless compound, namely, the cyclic carboxamide, as illustrated by the following wherein A is Br⊖ and R³ is methyl.

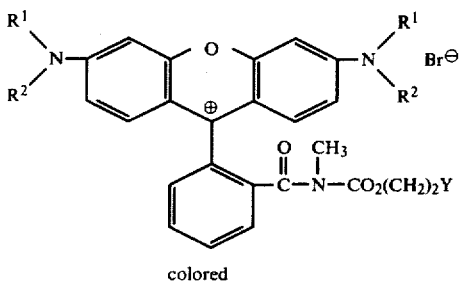

colored

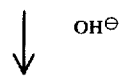

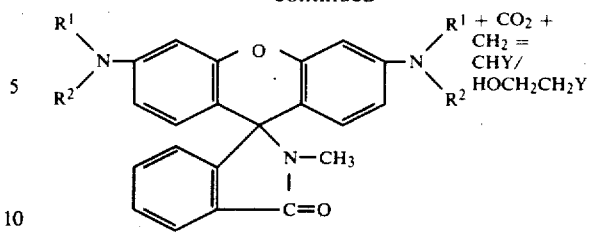

It will be appreciated that the by-products formed upon cleavage of the R³ group also are colorless. Because the said cleavage reaction proceeds at a faster rate at higher pH's, the subject compounds are particularly suitable for use in photographic processes where the pH is maintained above about 10 at least for the time necessary for decolorization to the corresponding ring-closed product.

The xanthene dyes of the present invention may be prepared, for example, (a) by reacting a compound of the formula

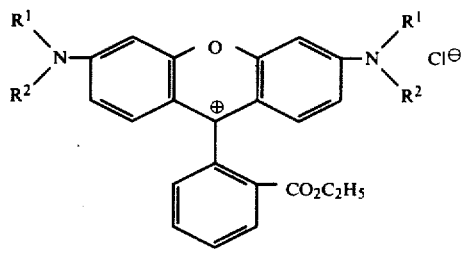

with a phenyl- or alkylamine to give the compound of the formula

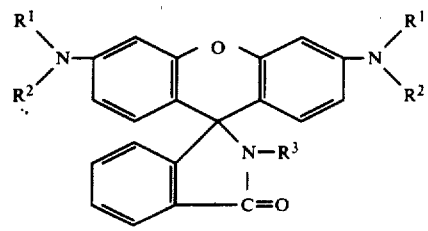

wherein R³ is alkyl or phenyl;

(b) treating the last-named compound with zinc in glacial acetic acid to give the compound of the formula

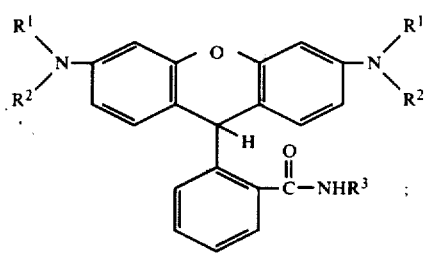

(c) reacting the last-named compound with the selected acrylating agent, for example, ClCO₂(CH₂)₂Y to give the leuco dye precursor of the formula

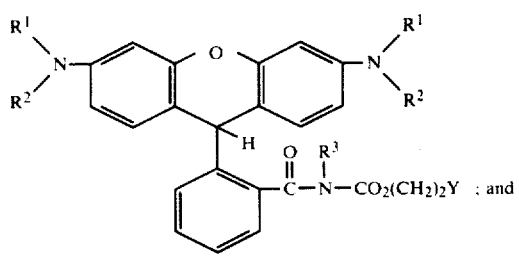

(d) oxidizing the leuco dye precursor with, for example, iodine or with, for example, o-chloranil and removing the dye product from its complex with o-chloranil with an acid to give the dye.

It will be appreciated that $R^1$, $R^2$ and Y in the foregoing reaction sequence have the same meaning as given in Formula I above.

The acylating agent may be prepared in a known manner by reacting the selected $HO(CH_2)_2Y$ with phosgene to give the corresponding $ClCO_2(CH_2)_2Y$.

The rhodamines used as starting materials in synthesizing the subject dyes may be prepared in a conventional manner, for example, as described in K. Venkataraman, The Chemistry of Synthetic Dyes, Vol. II, pp. 750-54, Academic Press Inc., N.Y. (1952).

The following Example is given to further illustrate the present invention and is not intended to limit the scope thereof.

EXAMPLE

Preparation of the compound having the formula

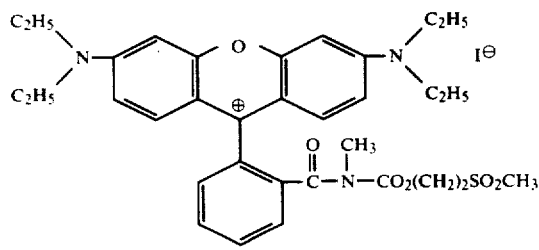

(a) To a solution of 7.5 g of the ethyl ester of Rhodamine B dissolved in 50 ml water was added 50 ml of 40% methylamine in water. The resulting solution was stirred for 4 hours during which time a pink solid precipitated and the deep magenta color disappeared. Another 50 ml of water was added to the flask and the solution was filtered. The solid was washed well with water and placed in a flask with 200 ml of acetone and heated to reflux until complete solution resulted. The solution was cooled and the white crystals were filtered. (yield 5.7 g) The mother liquor was evaporated to approximately 50 ml and allowed to stand. A second crop of 0.8 of solid was collected to give a total of 6.5 g of the compound

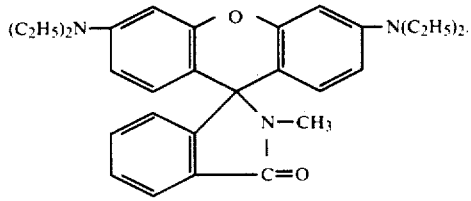

(b) One gram of the compound of step (a) was dissolved in glacial acetic acid under nitrogen. To this solution was added two spatulas of zinc, and then this reaction mixture was stirred well while heating on a steam bath. The magenta color disappeared with time and 25 ml of ether was added to the cooled solution. The zinc was filtered and washed with ether. A white solid then crystallized from the filtrate. More ether was added and filtered. A fluffy solid was filtered and vacuum dried to give 0.8 g of the compound

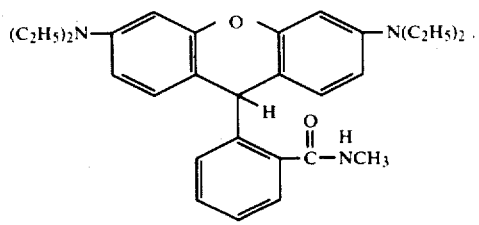

(c) A solution of 0.65 g of the compound of step (b) dissolved in 20 ml of tetrahydrofuran under nitrogen was cooled to −65° C. A solution of 1.6 M butyllithium in hexane (0.88 ml) was added dropwise and the mixture allowed to stir for one hour at −65° C. To this was added 0.53 g of $ClCO_2(CH_2)_2SO_2CH_3$ and the reaction mixture was stirred overnight. TLC on silica gel with 1/9 petroleum ether/ether showed mainly starting material. More of the chloroformate was added. Then the mixture was stirred but no further reaction occurred. The reaction mixture was poured into water and the precipitate removed by filtration. Preparative TLC on a sample of the light purple precipitate gave the leuco dye precursor

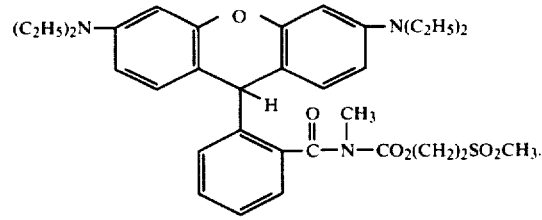

(d) The leuco dye precursor (50 mg) was dissolved in 10 ml of ethanol and air was bubbled through the light pink solution. Iodine (10 mg) was added, and a deep magenta developed. The solution was stirred for 2 hours. (TLC on silica gel with ether showed no starting material remaining. TLC on silica gel with 10% methanol/methylene chloride showed traces of other spots.) The reaction mixture was evaporated to dryness leaving the title compound as a purple solid.

The lactams of 2-[3,6-bis-diethylamino-9-anilinoxanthyl]benzoic acid and 2-[9-amino-3,6-bis-diethylaminoxanthyl] benzoic acid are disclosed in Beilstein's Handbuch der Organischen Chemie, Vol. 27, p. 431.

A sample of the dye prepared in the above Example was incorporated into the image-receiving layer 3 of an image-receiving component comprising the following layers.

A transparent 4 mil polyethylene terephthalate film base coated with, in succession:

1. as a polymeric acid layer, a mixture of about 9 parts of a partial butyl ester of polyethylene/maleic anhydride copolymer and 1 part of polyvinyl butyral coated at a coverage of about 2,500 mgs./ft.$^2$;
2. a timing layer containing a 14:1 ratio of a 60-30-4-6 tetrapolymer of butylacrylate, diacetone acrylamide, styrene and methacrylic acid and polyvinyl alcohol at a coverage of 500 mgs./ft.$^2$;
3. a graft copolymer of 4-vinylpyridine and vinylbenzyltrimethylammoniumchloride grafted on hydroxyethyl cellulose in a weight ratio of 2.2/1/2.2, respectively, coated at a coverage of 300 mgs./ft.$^2$ to provide an image-receiving layer.

The λmax of the dye as measured in the above-described image-receiving component was 568. When an aqueous 1 N sodium hydroxide solution was applied to the image-receiving layer of said image-receiving component, the dye was rendered colorless and remained colorless for at least 96 hours.

As a comparison, a dye compound of the formula

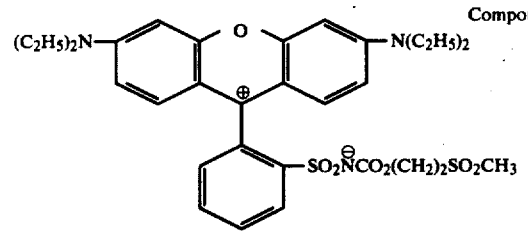

Compound A was incorporated into the image-receiving layer of an image-receiving element identical to that described above, the only difference being the use of ethanol as solvent. The λmax of compound A as measured in said image-receiving element was 567. When the image-receiving layer was treated with an aqueous solution approximately 1 N in sodium hydroxide, the dye was rendered colorless, but after about 15 minutes, a magenta color reappeared.

The compound of the above Example and Compound A undergo an irreversible cleavage reaction in aqueous alkaline solution at ambient temperature to give the new ring-closed cleavage products of the formulae

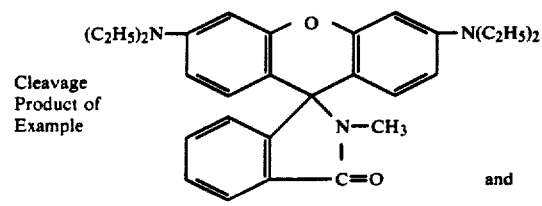

Cleavage Product of Example and

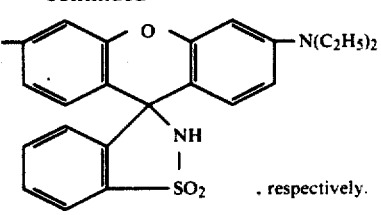

Cleavage Product of Compound A

, respectively.

As apparent from the above comparison, the ring-closed cleavage product of the compound of the Example remained colorless in the image-receiving element even after the environmental pH had been reduced below about pH 5.5 by said polymeric acid layer whereas the ring-closed cleavage product of Compound A became colored as the pH dropped.

In a further comparison, the approximate pH at which the above-denoted cleavage products became colored as the pH was reduced from alkaline to acid values was determined using pH buffers. It was found that the cleavage product of the subject dye remained colorless down to about pH 4, while the cleavage product of Compound A was faintly colored at pH 7 and became more intensely colored as the pH was reduced to about pH 4.

Though the alkyl/phenyl substituent on the N atom of the

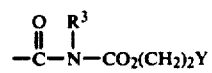

group is not essential to give a cleavage product that remains colorless as the pH is reduced, it is desirable to so substitute said N atom to increase the epsilon of the uncleaved dye to give a more highly colored compound.

Compound A was prepared by dissolving 477.6 mg (1.0 mM) of the compound

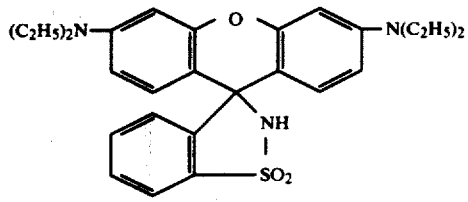

in 7.5 ml dry pyridine and then adding 205.3 mg (1.1 mM) of ClCO$_2$(CH$_2$)$_2$SO$_2$CH$_3$. The resulting reaction mixture was stirred at room temperature for about 16 hours at which time TLC showed that the reaction was about 65% complete. Another 200 mg of the chloroformate was added and the mixture stirred for another 6 hours at room temperature. (After 24 hours TLC showed the reaction substantially complete.) After additional stirring, the mixture was poured into 50 ml water, stirred for about 30 minutes and transferred to a separatory funnel. The mixture was extracted with methylene chloride (3×50 ml). The combined methylene chloride extracts were washed with water (2×50 ml), saturated sodium chloride (1×50 ml) and dried over sodium sulfate. The solvent was removed in vacuo leaving about 750 mg of residue. About 200 mg of the residue was dissolved in about 4 ml methylene chloride and using preparative TLC techniques, the product was separated and washed with acetone/methylene chloride. The acetone was removed in vacuo, and the product transferred to a 50 ml flask with methylene chloride. The methylene chloride was evaporated leaving 153 mg of Compound A.

As noted previously, the dyes of the present invention have the ability to decolorize completely and irreversibly in base by undergoing an irreversible cleavage reaction within a predetermined time at a predetermined pH to give a new colorless compound which remains colorless at the pH's normally encountered during processing subsequent to "bleaching" so that the new compound may be retained in a photographic film unit, e.g., a photosensitive element without the possibility of color reappearing in time. Typically, dyes may be selected for use as antihalation dyes, e.g., in a non-light-sensitive layer positioned intermediate a photosensitive silver halide emulsion layer and the support. Also, dyes may be selected for use as color correction filter dyes where absorption of light within a particular wavelength range during exposure is desirable for achieving appropriate color balance.

Illustrative film units in which the dyes of the present invention may be advantageously used as antihalation dyes are described, for example, in British Patent No. 1,482,156. These film units comprise, in the order in which incident light passes therethrough, an additive multicolor screen, a photosensitive silver halide emulsion layer, an antihalation layer in which the selected compound may be disposed, and preferably, an image-receiving layer. As described therein, exposure of the silver halide layer is accomplished through the screen which possesses optical filter elements selectively transmitting predetermined portions of incident radiation, e.g., red, green and blue light, to the underlying photosensitive silver halide layer. Upon photographic processing with an aqueous alkaline processing composition, soluble silver complex is transferred by diffusion and deposited in a superposed image-receiving layer as a function of the degree of exposure of silver halide behind each filter element. The silver image thus formed may then serve to modulate the quantity of light passing through the filter elements in the reverse direction during projection through a transparent support.

In a preferred embodiment, the image-receiving layer is intermediate the photosensitive silver halide emulsion layer and the additive multicolor screen and remains in position as part of an integral film unit prior to, during and after formation of the image. The antihalation dye is disposed in a processing composition permeable layer adjacent to the photosensitive layer on the side opposite the screen and serves to prevent the reflection or back-scattering of incident light which has passed through the photosensitive layer thereby eliminating the exposure of silver halide grains in the photosensitive layer other than those within the intended photoexposure path.

As noted above, the dyes of the present invention also are useful as color correction filter dyes in photographic film units comprising multilayered, multicolor photosensitive elements employing a blue-, a green-, and a red-sensitive silver halide layer, and particularly in integral negative-positive diffusion transfer film units wherein the image-receiving layer carrying the color transfer image is not separated from the developed photosensitive layers after processing but both components are retained together as a permanent laminate. Included as part of the laminate is a layer of light-reflecting material, preferably titanium dioxide, positioned between the image-carrying layer and the developed photosensitive layer(s). The light-reflecting layer separating the image-carrying and photosensitive components provides a white background for the transfer image and masks the developed photosensitive layer(s). In addition to these layers, the laminate usually includes dimensionally stable outer layers or supports, at least one of which is transparent so that the resulting transfer image may be viewed by reflection against the background provided by the light-reflecting layer.

Illustrative of patents describing such film units are U.S. Pat. No. 2,983,606 issued Mar. 9, 1961 to Howard G. Rogers, U.S. Pat. Nos. 3,415,644, 3,415,645 and 3,415,646 issued Dec. 10, 1968 to Edwin H. Land, U.S. Pat. Nos. 3,594,164 and 3,594,165 issued July 20, 1971 to Howard G. Rogers, and U.S. Pat. No. 3,647,437 issued Mar. 7, 1972 to Edwin H. Land. Copending U.S. Patent application Ser. No. 537,124 of Edwin H. Land, now abandoned, is concerned with multicolor diffusion transfer film units, wherein a layer of a dye, preferably a dye bleachable by the processing composition, is so positioned that photoexposure is effected therethrough, whereby said dye layer is effective as a color correction filter. For convenience, the specification of this application is specifically incorporated herein.

Whether used as antihalation dyes, color correction filter dyes or in other conventional photographic light-screening applications, the dyes of the present invention when disposed in a processing composition-permeable layer are completely and irreversibly decolorized by contacting with an aqueous alkaline processing composition for the time necessary for converting the colored dye compound to the new colorless ring-closed compound. The time required for decolorization, i.e., for conversion of the colored compound to the colorless product via said irreversible cleavage reaction may be measured at any given alkaline pH, and for a selected decoloration time, the pH of the processing composition contacted with and remaining in contact with the colored filter dye should be at least as high as that predetermined to give the selected decolorization time. In terms of T ½, the preferred compounds have a half-life (T ½) in approximately 1 N NaOH of about 30 seconds or less. By T ½ is meant the time measured for one-half of said colored dye to decolorize.

The dyes of the present invention may be incorporated into the appropriate layer of the photographic film unit using any of the techniques known in the art. For instance, the selected compound can be dissolved in the appropriate solvent and then dispersed, in the presence of a wetting agent if desired, in a coating solution containing a hydrophilic colloid binder, e.g., gelatin, and the resulting coating solution applied as the desired layer, for example, coated on a transparent support to provide an antihalation layer, or coated over the outermost photosensitive layer of a multilayered, multicolor photosensitive element to provide a color correction filter layer through which photoexposure is made. The concentration of compound in the layer will vary depending upon the product in which the filter layer is to be used and may be readily determined empirically to provide the optical density necessary for the specific use. It will be appreciated that the dyes of the present invention may be used in combination with each other and also may be used in combination with other classes of dyes previously employed in antihalation, color correction and other filter layers.

FIG. 1 of the accompanying drawing, which illustrates one embodiment of the present invention, is an enlarged cross-sectional view of an integral diffusion transfer film unit comprising a transparent film base or support 1 carrying on one surface, in order, additive multicolor screen 3 comprising a plurality of primary red color filter elements, a plurality of primary green color filter elements and a plurality of blue color filter elements arranged in a geometrically repetitive distribution in side-by-side relationship in substantially a single plane, photoinsensitive layer 5 carrying silver precipitating nuclei, photosensitive layer 7 containing silver halide crystals and antihalation layer 9 containing one or more light-screening dyes of the present invention.

As discussed in aforementioned British Patent No. 1,482,156, the degree of light absorption of the antihalation layer in such film units can vary over a relatively wide range, but usually, the antihalation layer possesses a transmission density range from about 0.4 to 1.4. Preferably, the transmission density is greater than 0.6 so that in the event a plurality of film units is employed in a stacked relationship during photoexposure, the antihalation layer will have sufficient density, i.e., light-absorbing capacity to substantially prevent reflectance as well as prevent exposure of underlying film units.

In determining the appropriate light-absorbing capacity for cyan, magenta and yellow for color correction purposes, "color compensating" filters as conventionally used in front of the camera lens may be employed in the usual manner as a convenient method of approximating the type and quantity of filtration which it would be desirable to provide. A layer containing the appropriate color correction dye(s) in a corresponding density may then be provided as a layer through which photoexposure is to be made.

Multicolor diffusion transfer images may be obtained using a variety of arrangements of the imagereceiving layer and the silver halide emulsions. Thus, these layers may be carried by a common support brought into superposition after photoexposure. A particularly advantageous film structure is shown in U.S. Pat. No. 3,415,644 wherein the requisite layers are in superposed relationship prior to and during photoexposure, and these layers are maintained in superposed relationship as a permanent laminate after processing and image formation. Such film units typically contain an outer transparent layer or support through which photoexposure is effected and the final multicolor image viewed, and another outer layer or support carrying at least the photosensitive layers, the latter support being opaque. While these supports or sheet-like elements may simply be held in superposed relationship, e.g., by a binding tape around the edges, in the preferred embodiment these elements are laminated together prior to photoexposure. This prelamination provides a number of benefits, both during manufacture and in photoexposure. Following exposure, the elements are delaminated by the distribution of a fluid processing composition which, upon solidification, bonds the elements together to form the desired permanent laminate. Procedures for forming such prelaminated film units wherein the two elements are temporarily laminated together prior to exposure are described, for example, in U.S. Pat. No. 3,625,231 to Albert J. Bachelder and Frederick J. Binda, and U.S. Pat. No. 3,652,282 to Edwin H. Land, both issued Mar. 28, 1972 and in U.S. Pat. No. 3,793,023 issued to Edwin H. Land on Feb. 19, 1974.

Figure 2:
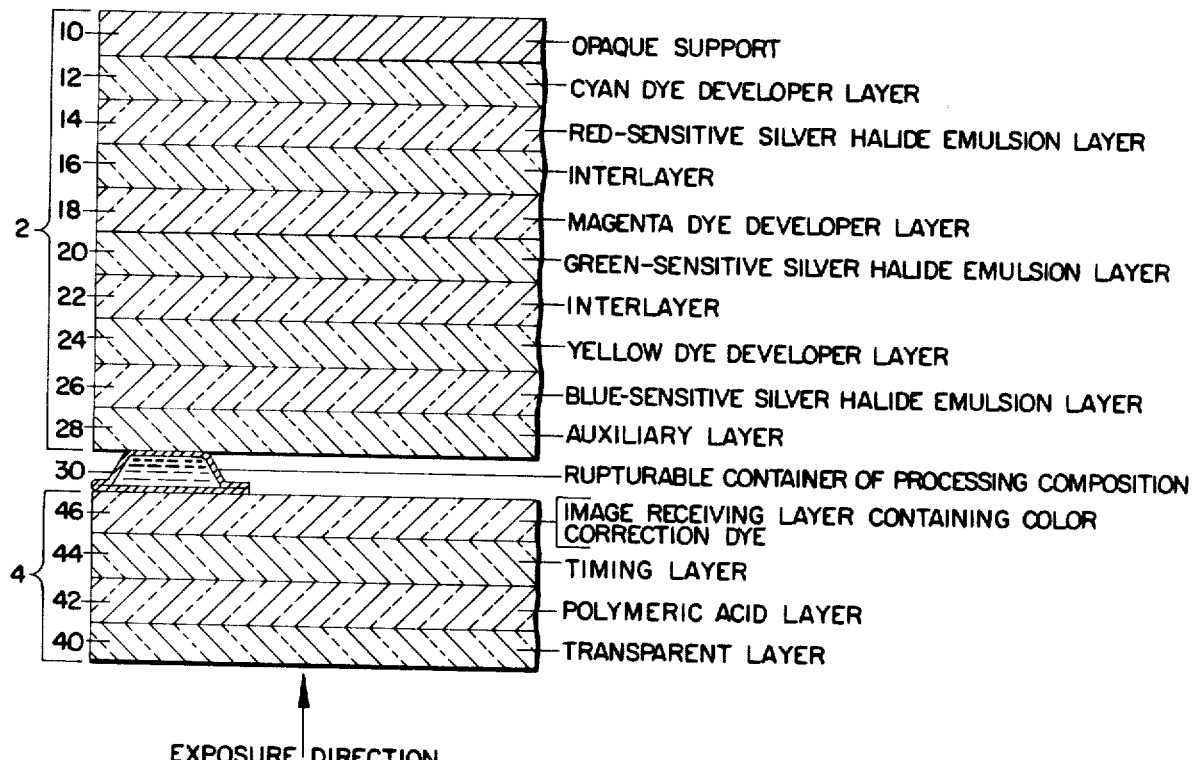
FIG. 2 is a diagrammatic, enlarged cross-sectional view of another diffusion transfer film unit incorporating a xanthene compound of the present invention as a color correction filter dye in the image-receiving layer.

Further description of this embodiment of the present invention may be facilitated by reference to FIG. 2 of the accompanying drawing which illustrates a diffusion transfer film unit adapted to provide integral negative-positive reflection prints and employing dye developers as the image dyes.

FIG. 2 illustrates a diffusion transfer film unit comprising a photosensitive element or component 2, a rupturable container 30, and an image-receiving element or component 4. The photosensitive element 2 comprises an opaque support 10 carrying, in turn, a cyan dye developer layer 12, a red-sensitive silver halide emulsion layer 14, an interlayer 16, a magenta dye developer layer 18, a green-sensitive silver halide emulsion layer 20, an interlayer 22, a yellow dye developer layer 24, a blue-sensitive silver halide emulsion layer 26, and an auxiliary layer 28. The positive or image-receiving element 4 comprises a transparent support 40 carrying, in turn, a polymeric acid layer 42, a timing layer 44 and an image-receiving layer 46 having dispersed therein a bleachable, light-screening dye of this invention as a color correction filter dye. The two elements are held in superposed, registered relationship, e.g., by a binding tape (not shown), so that photoexposure of the silver halide emulsion layers is effected through image-receiving layer 46 containing the bleachable dye. The rupturable container 30 contains a processing composition and is so positioned that, upon rupture the processing composition is distributed between the superposed elements 2 and 4. By including in the processing composition a light-reflecting pigment, preferably titanium dioxide, a light-reflecting layer may be provided against which the transfer image formed in the image-receiving layer 46 may be viewed. The developed photosensitive layers are masked from view by the light-reflecting layer and remain with the receiving layer 46 as part of a permanent laminate. The rupturable container 30 is of the type shown in U.S. Pat. No. 2,543,181 and is positioned adjacent the leading edge of the film unit.

In the processing of the film unit, the film unit is advanced relative to and between a pair of pressure-applying members which apply compressive pressure to the rupturable container 30 to eject its liquid contents between the photosensitive and image-receiving components 2 and 4 and then distribute the mass of liquid between the sheets toward the trailing ends thereof to form a layer of substantially uniform, predetermined thickness at least co-extensive with the image area. In order to insure sufficient processing liquid to form a layer of the required area and thickness between the sheets, excess processing liquid may be provided in container 30 and trapping means (not shown) provided for collecting and retaining excess processing liquid overrun. Details of the various layers of this and of the film unit of FIG. 1 may be found in the herein cited patents and applications and need not be recited here.

Processing of film units of the type described in FIG. 2 is initiated by distributing the processing composition between predetermined layers of the film unit. In exposed and developed areas, the dye developer will be immobilized as a function of development. In unexposed and undeveloped areas, the dye developer is unreacted and diffusible, and this provides an imagewise distribution of unoxidized dye developer, diffusible in the processing composition, as a function of the point-to-point degree of exposure of the silver halide layer. The desired transfer image is obtained by the diffusion transfer to the image-receiving layer of at least part of this imagewise distribution of unoxidized dye developer. In the illustrated embodiment, the pH of the photographic system is controlled and reduced by the neutralization of alkali after a predetermined interval, in accordance with the teachings of the above noted U.S. Pat. No. 3,615,644, to reduce the alkalinity to a pH at which the unoxidized dye developer is substantially insoluble and non-diffusible. As will be readily recognized, the details of such processes form no part of the present invention but are well known; the previously noted U.S. patents may be referred to for more specific discussion of such processes.

Multicolor images may be obtained by providing the requisite number of differentially exposable silver halide emulsions, and said silver halide emulsions are most commonly provided as individual layers coated in superposed relationship. Film units intended to provide multicolor images comprise two or more selectively sensitized silver halide layers each having associated therewith an appropriate image dye-providing material providing an image dye having spectral absorption characteristics substantially complementary to the light by which the associated silver halide is exposed. The most commonly employed negative components for forming multicolor images are of the "tripack" structure and contain blue-, green-, and red-sensitive silver halide layers each having associated therewith in the same or in a contiguous layer a yellow, a magenta and a cyan image dye-providing material respectively. Interlayers or spacer layers may, if desired, be provided between the respective silver halide layers and associated image dye-providing materials or between other layers. Integral multicolor photosensitive elements of this general type are disclosed in U.S. Pat. No. 3,345,163 issued Oct. 3, 1967 to Edwin H. Land and Howard G. Rogers as well as in the previously noted U.S. patents, e.g., in FIG. 9 of the aforementioned U.S. Pat. No. 2,983,606.

A number of modifications to the structures described in connection with FIG. 2 will readily suggest themselves to one skilled in the art. Thus, for example, the multicolor multilayer negative may be replaced by a screen-type negative as illustrated in U.S. Pat. No. 2,968,554 issued Jan. 17, 1961 to Edwin H. Land and in the aforementioned U.S. Pat. No. 2,983,606 particularly with respect to FIG. 3 thereof.

The image dye-providing materials which may be employed in such processes generally may be characterized as either (1) initially soluble or diffusible in the processing composition but are selectively rendered non-diffusible in an imagewise pattern as a function of development; or (2) initially insoluble or non-diffusible in the processing composition but which are selectively rendered diffusible or provide a diffusible product in an imagewise pattern as a function of development. These materials may be complete dyes or dye intermediates, e.g., color couplers. The requisite differential in mobility or solubility may, for example, be obtained by a chemical action such as a redox reaction or a coupling reaction.

As examples of initially soluble or diffusible materials and their application in color diffusion transfer, mention may be made of those disclosed, for example, in U.S. Pat. Nos. 2,774,668; 2,968,554; 2,983,606; 3,087,817; 3,185,567; 3,230,082; 3,345,163; and 3,443,943. As examples of initially non-diffusible materials and their use in color transfer systems, mention may be made of the materials and systems disclosed in U.S. Pat. Nos. 3,185,567; 3,719,489; 3,443,939; 3,443,940; 3,227,550; 3,227,552; and 4,076,529. Many types of image dye-providing substances and film units useful therewith also are discussed in the aforementioned U.S. Pat. No. 3,647,437 to which reference may be made.

It is also to be understood that "direct positive" silver halide emulsions may also be used, depending upon the particular image dye-providing substances employed and whether a positive or negative color transfer image is desired.

A preferred opacification system to be contained in the processing composition to effect processing outside of a camera is that described in the above-mentioned U.S. Pat. No. 3,647,437, and comprises a dispersion of an inorganic light-reflecting pigment which also contains at least one light-absorbing agent, i.e., optical filter agent, at a pH above the pKa of the optical filter agent in a concentration effective when the processing composition is applied, to provide a layer exhibiting optical transmission density > than about 6.0 density units with respect to incident radiation actinic to the photosensitive silver halide and optical reflection density < than about 1.0 density units with respect to incident visible radiation.

In lieu of having the light-reflecting pigment in the processing composition, the light-reflecting pigment used to mask the photosensitive strata and to provide the background for viewing the color transfer image formed in the receiving layer may be present initially in whole or in part as a preformed layer in the film unit. As an example of such a preformed layer, mention may be made of that disclosed in U.S. Pat. No. 3,615,421 issued Oct. 26, 1971 and in U.S. Pat. No. 3,620,724 issued Nov. 16, 1971, both in the name of Edwin H. Land. The reflecting agent may be generated in situ as is disclosed in U.S. Pat. Nos. 3,647,434 and 3,647,435, both issused Mar. 7, 1972 to Edwin H. Land.

The dye developers (or other image dye-providing substances) are preferably selected for their ability to provide colors that are useful in carrying out subtractive color photography, that is, the previously mentioned cyan, magenta and yellow. They may be incorporated in the respective silver halide emulsion or, in the preferred embodiment, in a separate layer behind the respective silver halide emulsion. Thus, a dye developer may, for example, be in a coating or layer behind the respective silver halide emulsion and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Dye developers, as noted above, are compounds which contain the chromophoric system of a dye and also a silver halide developing function. By "a silver halide developing function" is meant a grouping adapted to develop exposed silver halide. A preferred silver halide development function is a hydroquinonyl group. Other suitable developing functions include ortho-dihydroxyphenyl and ortho- and para-amino substituted hydroxyphenyl groups. In general, the development function includes a benzenoid developing function, that is, an aromatic developing group which forms quinonoid or quinone substances when oxidized.

The image-receiving layer may comprise one of the materials known in the art, such as polyvinyl alcohol, gelatin, etc. It may contain agents adapted to mordant or otherwise fix the transferred image dye(s). Preferred materials comprise polyvinyl alcohol or gelatin containing a dye mordant such as poly-4-vinylpyridine, as disclosed in U.S. Pat. No. 3,148,061 and graft copolymers containing 4-vinylpyridine as disclosed in U.S. Pat. No. 3,756,814.

In the various color diffusion transfer systems which have previously been described and which employ an aqueous alkaline processing fluid, it is well known to employ an acid-reacting reagent in a layer of the film unit to lower the environmental pH following substantial dye transfer in order to increase the image stability and/or to adjust the pH from the first pH at which the image dyes are diffusible to a second (lower) pH at which they are not. For example, the previously mentioned U.S. Pat. No. 3,415,644 discloses systems wherein the desired pH reduction may be effected by providing a polymeric acid layer adjacent the dyeable stratum. These polymeric acids may be polymers which contain acid groups, e.g., carboxylic acid and sulfonic acid groups, which are capable of forming salts with alkali metals or with organic bases; or potentially acid-yielding groups such as anhydrides or lactones. Preferably the acid polymer contains free carboxyl groups. Alternatively, the acid-reacting reagent may be in a layer adjacent to the silver halide most distant from the image-receiving layer, as disclosed in U.S. Pat. No. 3,573,043 issued Mar. 30, 1971 to Edwin H. Land. Another system for providing an acid-reacting reagent is disclosed in U.S. Pat. No. 3,576,625 issued Apr. 27, 1971 to Edwin H. Land.

An inert interlayer or spacer layer may be and is preferably disposed between the polymeric acid layer and the dyeable stratum in order to control or "time" the pH reduction so that it is not premature and interferes with the development process. Suitable spacer or "timing" layers for this purpose are described with particularity in U.S. Pat. Nos. 3,362,819; 3,419,389; 3,421,893; 3,455,686; and 3,575,701.

While the acid layer and associated spacer layer are preferably contained in the positive component employed in systems wherein the dyeable stratum and photosensitive strata are contained on separate supports, e.g., between the support for the receiving element and the dyeable stratum; or associated with the dyeable stratum in those integral film units, e.g., on the side of the dyeable stratum opposed from the negative components, they may, if desired, be associated with the photosensitive strata, as is disclosed, for example, in U.S. Pat. Nos. 3,362,821 and 3,573,043. In film units such as those described in the aforementioned U.S. Pat. Nos. 3,594,164 and 3,594,165, they also may be contained on the spreader sheet employed to facilitate application of the processing fluid.

As is now well known and illustrated, for example, in the previously cited patents, the liquid processing composition referred to for effecting multicolor diffusion transfer processes comprises at least an aqueous solution of an alkaline material, for example sodium hydroxide, potassium hydroxide, and the like, and preferably possessing a pH in excess of 12, and most preferably includes a viscosity-increasing compound constituting a film-forming material of the type which, when the composition is spread and dried, forms a relatively firm and relatively stable film. The preferred film-forming materials comprise high molecular weight polymers such as polymeric, water-soluble ethers which are inert to an alkaline solution such as, for example, a hydroxyethyl cellulose or sodium carboxymethyl cellulose. Other film-forming materials or thickening agents whose ability to increase viscosity is substantially unaffected if left in solution for a long period of time also are capable of utilization. The film-forming material is preferably contained in the processing composition in such suitable quantities as to impart to the composition a viscosity in excess of 100 cps, at a temperature of approximately 24° C. and preferably in the order of 100,000 cps to 200,000 cps at that temperature.

In particularly useful embodiments, the transparent polymeric support contains a small quantity of a pigment, e.g., carbon black, to prevent fog formation due to light-piping by internal reflection within the transparent support, and subsequent exiting from the support surface carrying the photographic layers, of actinic light incident upon an edge thereof; such elements are described in Belgian Patent No. 777,407. The transparent support advantageously may include an ultraviolet light absorber.

For purposes of illustrating the invention, a solution of a sample of the compound of the Example was incorporated into the image-receiving layer 3 of an image-receiving component comprising the structure set forth below by mixing the solution of the compound with a solution of the graft copolymer and coating this mixture on top of the timing layer to complete the image-receiving component.

A transparent 4 mil polyethylene terephthalate film base coated with, in succession:

1. as a polymeric acid layer, a mixture of about 9 parts of a partial butyl ester of polyethylene/maleic anhydride copolymer and 1 part of polyvinyl butyral coated at a coverage of about 2,500 mgs./ft.$^2$;
2. a timing layer containing a 14:1 ratio of a 60-30-4-6 tetrapolymer of butyacrylate, diacetone acrylamide, styrene and methacrylic acid and polyvinyl alcohol at a coverage of 500 mgs./ft.$^2$;
3. a graft copolymer of 4-vinylpyridine and vinylbenzyltrimethylammoniumchloride grafted on hydroxyethyl cellulose in a weight ratio of 2.2/1/2.2, respectively, coated at a coverage of 300 mgs./ft.$^2$ to provide an image-receiving layer and containing the selected dye compound.

The image-receiving component containing the dye compound was placed on a piece of gelatin coated Mylar, and the transmission densities for red (R), green (G) and blue (B) were recorded on a transmission densitometer. Then several drops of aqueous 1 N KOH were added to the gelatin sheet, and the image-receiving component was lightly pressed against the gelatin sheet to "bleach" the dye compound. After about 60 seconds, the transmission densities were again recorded for red (R), green (G) and blue (B) for the "sandwich". The results are set forth below.

| Transmission Densities | | | | | |
|---|---|---|---|---|---|
| Before Bleaching | | | After Bleaching | | |
| R | G | B | R | G | B |
| .01 | .15 | .00 | .02 | .01 | .01 |

The densitometer was set at 0.00 for R, G, B with two pieces of gelatin coated Mylar in the light beam.

From these results, it can be seen that the subject dyes are effective in absorbing radiation within a certain wavelength range, and when treated with aqueous alkali are "bleached", i.e., decolorized.

It will be appreciated that various solvents may be employed for dispersing the dyes in the image-receiving or other appropriate layer of the photographic product and that useful solvents may be readily selected for a given compound. Also, it will be understood that where the anion may possibly have an adverse effect on the photosensitive material, the dye will be positioned other than in the silver halide emulsion layer(s), and depending upon the mobility of the dye in a given matrix or binder, it may be desirable to employ an immobilizing group or a group that will mordant to the matrix to prevent migration of the dye, particularly, where the photographic product is subjected to conditions of high temperature and high humidity prior to use.

Also, it will be appreciated that in utilizing the subject dyes to correct color balance, for example, in multicolor diffusion transfer photographic film units that a photosensitive element may be exposed to a suitable multicolor step-wedge and diffusion transfer processed with a given processing composition and image-receiving element. The blue, green and red D log E curves of the resulting multicolor transfer image (sample image) are then prepared. Examination of these D log E curves will indicate to one skilled in color photographic sensitometry the manner and extent to which the individual D log E curves depart from the desired curve shape. From this examination, one may determine by routine analysis and experimentation how much filtration would be required of what wavelength range or ranges to obtain a more desirable color balance. The photosensitive element of another film unit, having the identical photosensitive element, image-receiving element and processing composition as used in obtaining the sample image, is then given the same exposure through a conventional color correction filter(s) of the color and density estimated to be necessary to provide the desired changes in the D log E curves of the sample image. The blue, green and red D log E curves of the resulting test multicolor transfer image are then prepared and compared with the sample. While more than one "test" may be required to determine the color filtration most effective to give the desired D log E curve shape changes, such tests may be performed rapidly and easily. When the appropriate color filtration has been determined, a layer containing a color correction dye or dyes absorbing light in appropriate wavelength range(s) is coated on a transparent support at a coverage calculated to provide the requisite density. This "test" color correction dye layer is placed in the exposure path and the previous exposure test repeated. Analysis of the D log E curves of the resulting multicolor transfer image will indicate what changes, if any, should be made in the spectral absorption range and density prior to incorporating a corresponding color correction dye layer into the diffusion transfer film unit.

It will be recognized that effecting photoexposure through a layer containing the subject dye(s) is effective to "filter", i.e., decrease the exposure given to the silver halide layer(s) exposable by light absorbed by said color correction dye(s) and that one or more dyes of the present invention may be used in conjunction with other filter dyes for effecting changes in one, two or all three of the individual red, green and blue H and D curves to achieve the desired color balance. Though the subject dyes find particular utility in diffusion transfer and other photographic film units where it is desired to bleach the dye(s) during processing subsequent to photoexposure through the dye layer(s), the subject dyes also may be employed in diffusion transfer and other film units where the dye is so positioned as not to contribute dye density to the transfer or final image. Where the filter dye layer through which photoexposure has been made is not part of the transfer image, or where the final image is masked from view as in certain integral negative-positive reflection print structures, the "unbleached" filter dye should be non-diffusible to the image-receiving layer containing the transfer image. The requisite non-diffusion character may be provided by the use of a suitable mordant, by the use of long chain "ballast" or "anchor" substituents and/or other art known techniques.

As noted in the above example, in integral diffusion transfer film units, the color correction dye(s) may be incorporated in the image-receiving layer. The choice of location of the color correction dye(s) will depend in large part upon what stage of the manufacturing process the determination is made to incorporate such a color correction dye. As will be readily apparent, provision of the color correction dye(s) in a separate lsyer has the advantage of permitting modification after the components have fully "matured" and also permits different modification of portions of the same lot of the positive component.

The supports for the various layers may be any of the types known in the art to be useful. In the preferred embodiments wherein an integral negative-positive reflection print is obtained, the supports should be dimensionally stable and may be polyethylene terephthalate or other polymeric film base, as disclosed in the cross-referenced patents.

It will be recognized that the transfer image formed following exposure and processing of film units of the type illustrated in FIG. 2 will be a geometrically reversed image of the subject. Accordingly, to provide geometrically non-reversed transfer images, exposure of such film units should be accomplished through an image reversing optical system, such as in a camera possessing an image reversing optical system utilizing mirror optics, e.g., as described in U.S. Pat. No. 3,447,437 issued June 3, 1969 to Douglas B. Tiffany.

Where the expression "positive image" has been used, this expression should not be interpreted in a restrictive sense since it is used primarily for purposes of illustration, in that it defines the image produced on the image-carrying layer as being reversed, in the positive-negative sense, with respect to the image in the photosensitive emulsion layers. As an example of an alternative meaning for "positive image", assume that the photosensitive element is exposed to actinic light through a negative transparency. In this case, the latent image in the photosensitive emulsion layers will be positive and the dye image produced on the image-carrying layer will be negative. The expression "positive image" is intended to cover such an image produced on the image-carrying layer, as well as transfer images obtained by use of direct positive silver halide emulsions to provide a "positive" image of the photographed subject.

While the usefulness of the subject xanthene dyes has been illustrated as applied to integral diffusion transfer film units where the transfer image is retained with the developed photosensitive element as part of a permanent laminate, it will be understood that the xanthene dyes of this invention also may be used to provide antihalo, color correction or other light filtering layer(s) in diffusion transfer film units where the transfer image, either in silver or in dye, is separated from the developed photosensitive layer(s) subsequent to processing. Though the image dye-providing materials are preferably dye developers, it will be appreciated that other types of image dyes and dye intermediates may be employed to provide the dye transfer image.

Besides their usefulness in diffusion transfer photographic products and processes, the xanthene dyes of the present invention also may be used in filter layers of conventional photographic materials, for example, in antihalation or color correction layers in conventional negatives, and may be disposed in the appropriate layer(s) in an amount sufficient to provide the desired filtering effect. The selection and incorporation of the xanthene dye for the desired filtering effect may be accomplished in a known manner using conventional techniques and is well within the skill of the art. For example, for color correction purposes, the dye(s) selected may absorb light within a specific wavelength range, e.g., blue, green or red light, or within a combination of several wavelength ranges and will be disposed in a layer through which photoexposure is made. Indeed, it may be desirable in a given instance to filter light of two different wavelength ranges in a ratio such that one silver halide emulsion receives more exposure filtration than does another. As in the diffusion transfer film units, the dye(s) selected for color correction are advantageously applied after the photosensitive element has aged to "maturity", i.e., the sensitometry of the photosensitive element as manufactured is no longer changing significantly with time. Where the subject dyes are employed for antihalation purposes, they may be incorporated, for example, in a layer on one or both sides of a support carrying the photosensitive layer(s) and where they are employed as optical filter agents, they will be so positioned as to prevent post-exposure fogging during processing in ambient light without, of course, interfering with imagewise exposure of the photosensitive layer(s) or with viewing of the final image.

Since certain changes may be made in the hereinafter defined subject matter without departing from the scope of the invention herein involved, it is intended that all matter contained in the above description and examples be interpreted as illustrative and not in a limiting sense.

What is claimed is:

1. A compound of the formula

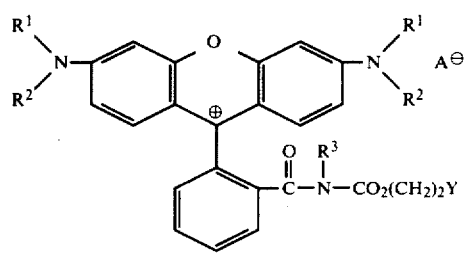

wherein each $R^1$ the same or different is hydrogen or alkyl having 1 to 4 carbon atoms, each $R^2$ the same or different is alkyl or phenyl having 1 to 4 carbon atoms, $R^3$ is phenyl or alkyl having 1 to 4 carbon atoms, Y is an electron-withdrawing group having a positive sigma value greater than 0.6 as defined by Hammett's Equation, and A is an anion.

2. A compound as defined in claim 1 wherein each $R^1$ is alkyl.

3. A compound as defined in claim 1 wherein each $R^2$ is alkyl.

4. A compound as defined in claim 1 wherein $R^3$ is alkyl.

5. The compound

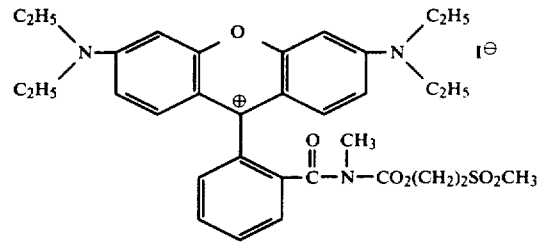

6. A compound as defined in claim 4 wherein said alkyl is methyl.